(12) United States Patent
Lloyd et al.

(10) Patent No.: US 6,409,662 B1
(45) Date of Patent: Jun. 25, 2002

(54) PATIENT INTERFACE SYSTEM

(75) Inventors: Lester John Lloyd, Orinda, CA (US); Melissa Ann Prince, Winchester, KY (US)

(73) Assignee: Alere Medical, Inc., Concord, CA (US)

( * ) Notice: Subject to any disclaimer, the term of this patent is extended or adjusted under 35 U.S.C. 154(b) by 0 days.

(21) Appl. No.: 09/399,982

(22) Filed: Sep. 20, 1999

Related U.S. Application Data

(63) Continuation of application No. 08/958,689, filed on Oct. 28, 1997, now Pat. No. 6,080,106.

(51) Int. Cl.$^7$ ................................................. A61B 5/00
(52) U.S. Cl. ....................... 600/300; 128/904; 340/573; 340/665
(58) Field of Search ................................. 600/300–301, 600/483, 513, 520; 128/903–904, 920–925; 705/2–3; 340/500, 540, 573, 666; 200/666, 85 R, 86 R

(56) References Cited

U.S. PATENT DOCUMENTS 5,588,440 A * 12/1996 Cowie .......................... 600/587
6,206,829 B1 * 3/2001 Iliff .............................. 600/300

* cited by examiner

*Primary Examiner*—Kevin Shaver
*Assistant Examiner*—Michael C Astorino
(74) *Attorney, Agent, or Firm*—Karl Bozicevic; Paula A. Borden; Bozicevic, Field & Francis, LLP.

(57) ABSTRACT

A patient interface system for collecting and transferring data from a patient to a remote monitoring system, as well as methods for its use, are provided. The subject system comprises: (a) a data collection means comprising an edema sensing means and an interrogation means; (b) a processing means for processing the collected data; and (c) a communication means for transferring said collected data from said interface means to a remote monitoring system and receiving instructional data from a remote monitoring system. The subject system finds use in the remote monitoring of a variety of conditions, particularly in the remote monitoring of cardiac associated diseases.

28 Claims, 10 Drawing Sheets

Probe Flush With Plate

Probe Pressed Into Skin

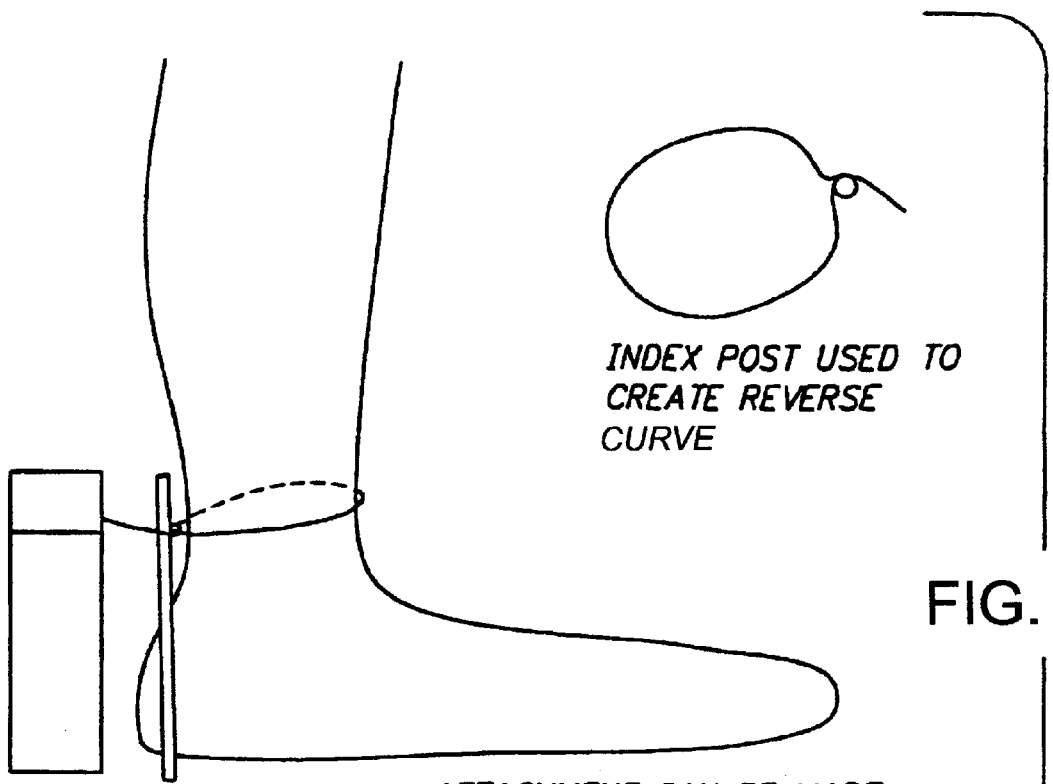
INDEX POST USED TO CREATE REVERSE CURVE
INDEX POST
ATTACHMENT CAN BE MADE TO CABEL ITSELF OR TO POST
FIG. 14
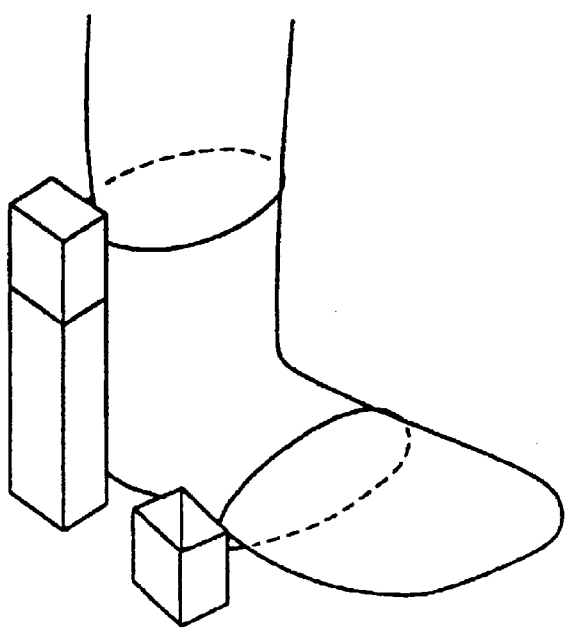
PREF. EMBODIMENT USES TWO MEASUREMENTS

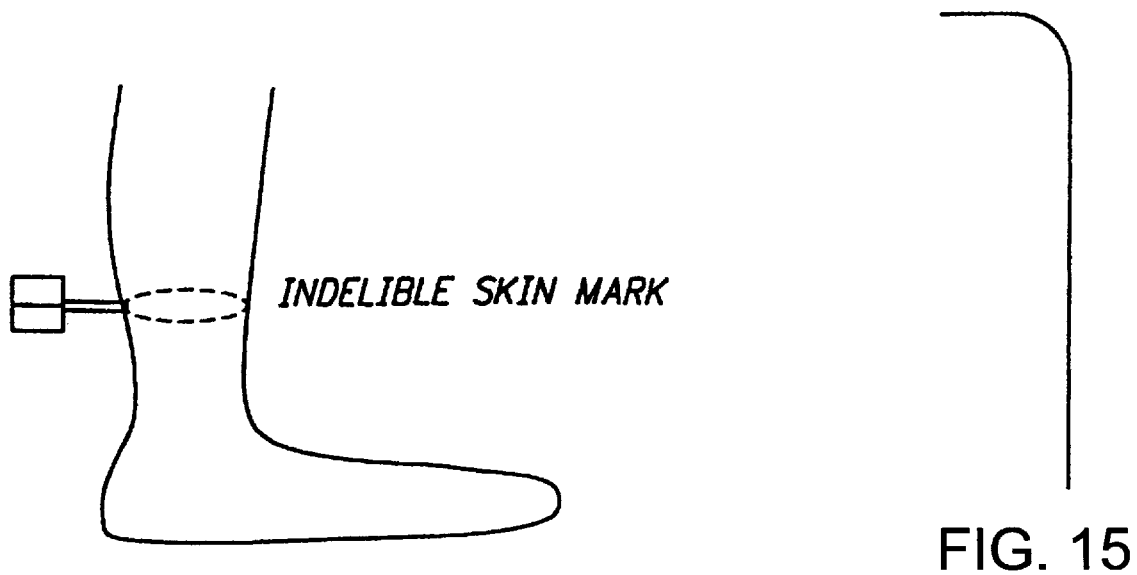
USE OF PORTABLE MODEL
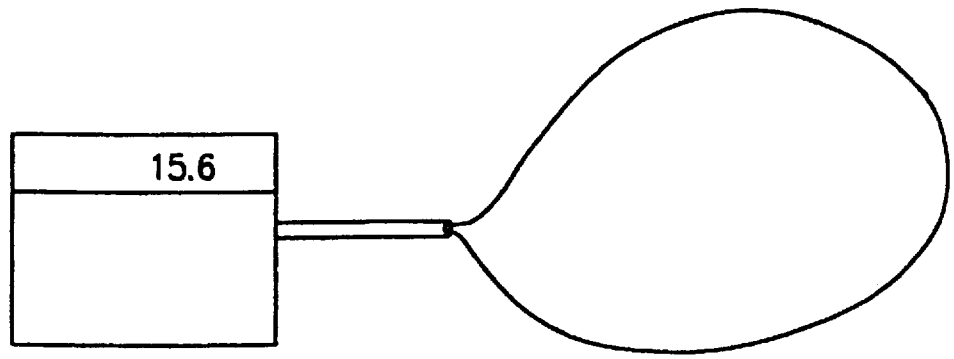
15.6
PORTABLE MODEL FEEDS CABLE THRU A TUBE TO GENERATE A SINGLE CONTACT POINT – LOCAL ELECTRONICS
INDELIBLE SKIN MARK
FIG. 15

PATIENT INTERFACE SYSTEM

CROSS-REFERENCE

This application is a continuation application of Serial No. 08/958,689, now U.S. Pat. No. 6,080,106 filed Oct. 28, 1997, which is incorporated herein by reference in its entirety and to which application we claim priority under 35 USC §120.

FIELD OF THE INVENTION

The field of this invention is patient monitoring systems.

BACKGROUND OF THE INVENTION

Frequent monitoring of patients permits the patients' physician to detect worsening symptoms as they begin to occur, rather than waiting until a critical condition has been reached. As such, home monitoring of patients with chronic conditions is becoming increasingly popular in the health care industry for the array of benefits it has the potential to provide. Potential benefits of home monitoring are numerous and include: better tracking and management of chronic disease conditions, earlier detection of changes in the patient condition, and reduction of overall health care expenses associated with long term disease management. The home monitoring of a number of diverse "chronic diseases" is of interest, where such diseases include diabetes, dietary disorders such as anorexia and obesity, respiratory diseases, AIDS and other chronic viral conditions, conditions associated with the long term use of immunosuppressants, e.g. in transplant patients, asthma, chronic hypertension, chronic use of anticoagulants, and the like.

Of particular interest in the home monitoring sector of the health care industry is the remote monitoring of patients with heart failure (HF), also known as congestive heart failure. HF is a syndrome in which the heart is unable to efficiently pump blood to the vital organs. Most instances of HF occur because of a decreased myocardial capacity to contract (systolic dysfunction). However, HF can also result when an increased pressure-stroke-volume load is imposed on the heart, such as when the heart is unable to expand sufficiently during diastole to accommodate the ventricular volume, causing an increased pressure load (diasystolic dysfunction). In either case, HF is characterized by diminished cardiac output and/or damming back of blood in the venous system. In HF, there is a shift in the cardiac function curve and an increase in blood volume caused in part by fluid retention by the kidneys. Indeed, many of the significant morphologic changes encountered in HF are distant from the heart and are produced by the hypoxic and congestive effects of the failing circulation upon other organs and tissues. One of the major symptoms of HF is edema, which has been defined as the excessive accumulation of interstitial fluid, either localized or generalized.

Edema is defined as the abnormal accumulation of fluid in connective tissue. Edema typically results from a combination of passive venous congestion and salt and water retention, and may be systemic or localized to a particular region of the body. Dependent edema, in which fluid accumulates in the tissues of the limbic extremities, e.g. ankle, foot and the like, is a physical manifestation of a number of different human disease conditions. Dependent edema first appears in the feet and ankles of the ambulatory patient, and in the posterior surface of the calves and skin overlying the sacrum in the bedridden patient. Disease conditions characterized by the presence of dependent edema include local venous or lymphatic obstruction, cirrhosis, hypoalbumenia, and congestive heart failure.

In congestive heart failure, the presence of edema in the lower extremities is a valuable diagnostic marker for the presence of the disease. In addition to serving as a marker for the presence of congestive heart failure, the progression of the edemic state can be monitored over time and the progression of the edemic state related to the progression of the disease.

One way of detecting the presence of edema is to determine fluid volume change of the patient. A number of different technologies have been developed to identify the volume change, and include those based on the use of water or air-filled cuffs, mercury strain gauge, fiber optic strain gauge, and airborne ultrasound. Such technologies have principally been employed to measure venous blood flow and to sense the volume pulsations created by the heart.

Another way of detecting the presence of edema is the "pitting" method. In this method, a physician's thumb or finger is pressed into the patient's skin next to a bony surface (e.g., tibia, fibula, or sacrum). When the physician's finger is withdrawn, an indentation persists for a short time. The depth of the "pit" is estimated and generally recorded in millimeters, although subjective grading systems (e.g. "+++", etc.) have also been described. In general, the distribution of edema is also noted, as the amount of fluid is roughly proportional to the extent and the thickness of the pit.

HF is the most common indication for hospitalization among adults over 65 years of age, and the rate of admission for this condition has increased progressively over the past two decades. It has been estimated that HF affects more than 3 million patients in the U.S. (J. B. O'Connell et al., J. Heart Lung Transpl. (1993) 13(4):S107–112).

In the conventional management of HF patients, where help is sought only in crisis, a cycle occurs where patients fail to recognize early symptoms and do not seek timely help from their care-givers, leading to emergency department admissions (Miller, P. Z., 1995, "Home monitoring for congestive heart failure patients," Caring Magazine, August 1995: 53–54). Recently, a prospective, randomized trial of 282 patients was conducted to assess the effect of the intervention on the rate of admission, quality of life, and cost of medical care. In this study, a nurse-directed, multi disciplinary intervention (which consisted of comprehensive education of the patient and family, diet, social-service consultation and planning, review of medications, and intensive assessment of patient condition and follow-up) resulted in fewer readmissions than the conventional treatment group and a concomitant overall decrease in the cost of care (M. W. Rich et al., New Engl. J. Med. (1995) 333:1190–95). Similarly, comprehensive discharge planning and a home follow-up program was shown to decrease the number of readmissions and total hospital charges in an elderly population (M. Naylor et al., Amer. College Physicians (1994) 120:999–1006). Therefore, home monitoring is of particular interest in the HF management segment of the health care industry.

Another area in which home-monitoring is of particular interest is in the remote monitoring of a patient parameter that provides information on the titration of a drug, particularly with drugs that have a consequential effect following administration, such as insulin, anticoagulants, ACE inhibitors, β-blockers, etc.

Although a number of different home monitoring systems have been developed, there is continued interest in the development of new monitoring systems. Of particular interest would be the development of a system that provides for improved patient compliance, ease of use, etc. Of more particular interest would be the development of such a system that is particularly suited for use in the remote monitoring of patients suffering from HF.

Relevant Literature

Monitoring systems are described in U.S. Pat. Nos. 5,241, 965; 5,549,117; 5,584,297; 5,307,263; 4,803,625; 4,546, 436; 5,007,429; 5,019,974; 5,077,476; 5,182,707; 4,838, 275; as well as in Capone et al., Am. Heart J. (1988) 116: 1606; Chadda et al., Am. Heart J. (1986) 112: 1159; Fleg et al., Arch. Intern. Med. (1989) 149:393; Katz et al., Obstetrics & Gynecology (1986)68:773; Patel et al., J. Med. Sys. (1992) 16: 101.

Scientific American Medicine (Dale & Freeman eds)1:II provides a review of heart failure, physical manifestations and methods for the treatment thereof.

Lindahl & Omata, Med. Biol. Eng. Comput. (1995) 33:27–32 provide a description of methods of assessing edema.

Other references of note include U.S. Pat. Nos.: 3,791, 375; 3,890,958; 3,974,491; 4,144,749; 4,383,533; 5,052, 405; 5,323,650; and 5, 385,069; as well as Swedborg, Scand. J. Rehab. Med. (1977) 9:131–135; Mridha & Odman, Scand. J. Rehab. Med. (1989)21:63–39; Mridha & Ödman, Med. Biol. Eng. Comput. (1986) 24: 393–398; Kushner et al., Am. J. Clin. Nut. (1986) 44: 417–424; Breytenbach, Int. J. Oral Surg. (1978) 7:386–392; Davies et al., Med. Biol. Eng. Comput. (1971) 9:567–570; Lindhal et al., Med. Biol. Eng. Comput. (1991) 29: 591597; Iwakura, Med. Biol. Eng. Comput. (1978) 16:429–436; and Starr, BPR (1980) 17:98–102.

SUMMARY OF THE INVENTION

A patient interface system for collecting and transferring data from a patient to a remote monitoring system, and methods for its use in the management of a chronic condition, are provided. The subject interface system includes: (a) a patient data input means having both a sensor and a question and answer means; (b) a processing means; and (c) a communication means for transferring data to and from a remote monitoring means. Also provided is a patient monitoring system comprising the subject patient interface means operationally linked to the remote monitoring system. The subject patient interface system finds use in a variety of applications in which the condition of a patient is monitored remotely, and is particularly suited for use in the remote monitoring of patients suffering from a cardiac associated disease.

The patient interface system is particularly adapted for measuring edema of a patient on a daily basis. Data obtained from each measurement are transmitted to a central processing location for analysis. The system is designed so that it can receive and process data from a plurality of different patients at a plurality of different locations. The data are analyzed to determine if additional action is needed, e.g., obtain additional data via specific questions posed to the patient(s) and/or instruct the patient(s) to obtain medical assistance.

These and other objects, advantages, and features of the invention will become apparent to those persons skilled in the art upon reading the details of the patient interface system, as more fully described below.

BRIEF DESCRIPTION OF THE DRAWINGS

FIG. 14 depicts the measurement of a limb using a reference rod.

FIG. 15 depicts the measurement of a limb using a portable transducer fitted with a tube.

MODES OF CARRYING OUT THE INVENTION

Figure 1:
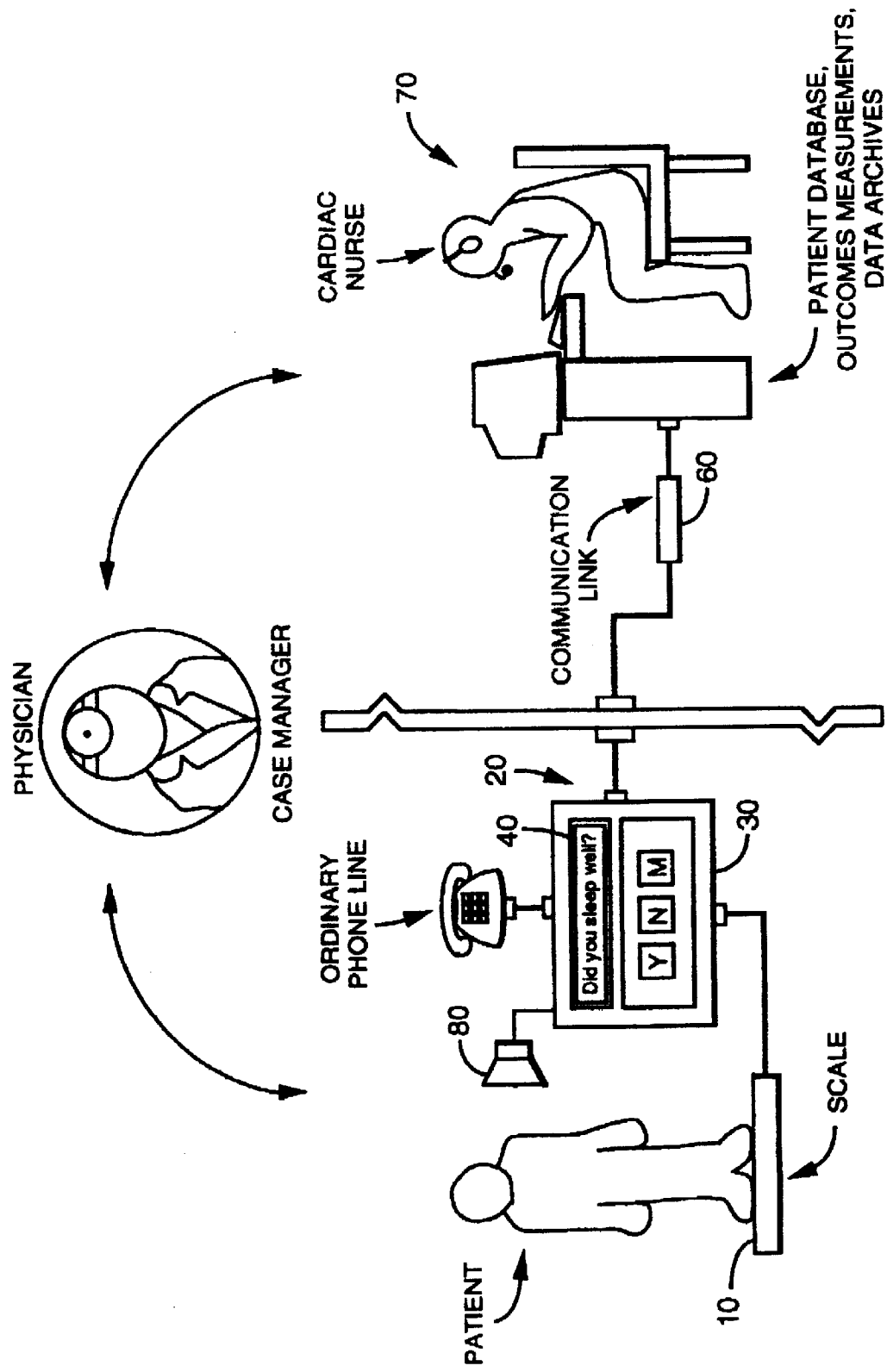
FIG. 1 provides a schematic of the interface system of the subject invention and its use in the remote monitoring of a patient with a cardiac associated disease.

A patient interface system for collecting and transferring data from a patient to a remote monitoring system is provided. The subject system includes:(a) a patient data input means comprising an edema measurement device and preferably other sensors or measuring means along with a question and answer means; (b) a processing means; and (c) a communication means for transferring data to and from a remote monitoring system. Also provided is a patient monitoring system comprising the subject patient interface means operationally linked to the remote monitoring system. The subject patient interface system finds use in a variety of applications in which the condition of a patient is monitored remotely, and is particularly suited for use in the remote monitoring of patients suffering from a cardiac associated disease.

Before the present patient interface system is described, it is to be understood that this invention is not limited to the particular interface system described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a means" includes a plurality of such means and reference to "the system" includes reference to one or more systems and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Patient Interface System

The subject patient interface system is suited for use in the collection and transfer of data from a patient having a condition to a remote monitoring system. The interface system of the invention may be used in the monitoring and management of a variety of different conditions, where such conditions include medically induced conditions, e.g. immunosuppression due to the chronic use of immunosuppressants as found in transplant patients, and naturally occurring disease conditions, such as diabetes, nutrition disorders, e.g. anorexia and obesity, AIDS and other virally associated conditions, asthma, chronic hypertension, chronic use of anticoagulants, and cardiac associated diseases, such as heart failure (HF), where the use of the subject interface system in the monitoring of patients with cardiac associated diseases is particularly preferred.

The first element of the subject interface system is the patient data input means that comprises both an edema measuring means and preferably an additional sensor such as a scale along with an active interrogation means, i.e. a "question and answer" means. The additional sensor is capable of measuring a parameter diagnostic of the patient's health, i.e. a "diagnostic parameter. As used herein, a "sensor" is any device capable of measuring a physical characteristic or attribute of the patient, particularly a parameter diagnostic of the patient's health or condition. A parameter is "diagnostic" if it provides a physician with significant information about the patient's condition. For example, weight, blood pressure, heart rate, temperature, and the like are all "diagnostic parameters" for some indications. It is preferred to employ a diagnostic parameter that correlates closely with the patient's condition, or any change in the patient's health. For example, HF patients may be monitored by following their degree of edema. Sensitive measurement of weight changes should correlate closely with edema, and may be used as a surrogate. Obese patients may be monitored by measuring their weight. Accordingly, the additional sensor may be any sensing means that is capable of measuring such parameters, such as a scale for measuring the patient's weight, or a means for measuring the patient's blood pressure, oxygen saturation, ECG, blood glucose level, and the like.

Preferred systems are designed for use in the monitoring of cardiac associated diseases, particularly HF, preferred are those embodiments of the subject invention comprising a means for sensing edema, particularly edema of an extremity, such as: (a) a volume displacement measurement means; (b) a cross-sectional dimension measurement means; (c) a pitting measurement means; and a circumferential measurement means. The system also preferably includes a weight detection means, such as a scale. These systems are described in more detail below.

In addition to the sensor component, the data input means of the subject interface system also comprises an active interrogation means or "question and answer" means for presenting the patient with one or more questions related to the patients health status and recording the patient's answers to the questions. Questions which may be presented by the interrogation means may be simple "yes" or "no" questions, or be more complicated, requiring a more descriptive response or a selection of one of a plurality responses. The particular questions presented to the patient by the interface system will be chosen in view of the particular condition being monitored, or the state or progression of the condition being monitored, where representative questions include: (1) "Were you tired during the day?"; (2) "On a scale of 1 to 5, 5 being most, how tired were you in the middle of the day?"; (3) "Did you cough during the night?"; (4) "Did you need an extra pillow to sleep?"; (5) "Are your shoes tighter than usual?"; (6) "Did you exercise today?"; and the like. The questions may vary depending on the time of day in which they are asked, as certain questions may be more relevant in the morning than in the evening, etc. In addition to question, instructions information in the form of directions or suggestions may be given to the patient, e.g. (1) "Please take your blood pressure."; (2) "Don't forget to take your medicine."

The interrogation means may take any convenient form. For example, the question and answer means may be an input panel, where the input panel may be as simple as a toggle switch or pair of push buttons (e.g., "Yes/No"), or may comprise a full keyboard or touch-screen input system. Alternatively, the interrogation means may comprise a microphone, preferably coupled with voice-recognition software, where such software is known in the art. Audio answers may be recorded and transmitted unaltered, may be compressed, or may be "recognized", and transmitted in the form of a corresponding text file. The questions are drafted with the interrogation means in mind. For example, if the interrogation means comprises a series of five pushbuttons, the patient may be asked, for example, to rate his or her hunger or thirst on a scale of 1 to 5. If a keyboard is provided, the patient may type in any answer desired: this gives greater freedom to the patient, but may make it more difficult to correlate and tabulate the patient's records. Alternatively, keyboard answers may be restricted to a limited set (e.g., the patient may still be required to pick "choice a", "choice b", etc.). Since the patient may be partially incapacitated, it is preferred to simplify the interrogation means as much as possible, either by providing for spoken input or by limiting choices to a few push buttons.

The interrogation means may further provide information and/or questions to the patient, typically either visually or audibly. The questions may be displayed on a standard CRT, LED or LCD display, or played audibly over a speaker. One may also use a combination of these means for the first output means. For example, one may provide an LED display of the patient's weight, along with "spoken" questions. The system may also be provided with an additional "alarm tone" to remind the patient when readings should be taken. It is preferred to present questions either audibly, or typed on an easily-readable display. The questions may be provided in a number of different languages, with the appropriate language selected by either the patient or the monitoring staff.

In a preferred embodiment, the patient data input means will be automatic, by which is meant that the patient does not need to take any active steps to activate the patient data input means, e.g. the patient does not have to turn the means "on." For example, where the sensor is a scale, the patient need only step onto the scale. The input means will then sense the presence of the patient on the scale, determine and record the patient's weight, and automatically present to the patient one or more questions and record the patient's answers thereto.

The next component of the interface system is the processor means. The processor means may comprise any processor having sufficient power to store and present data, and may range from a microprocessor to a personal computer. The processor processes the data collected by the patient data input means in some manner. The processor means is capable of at least the following tasks: capturing data from the sensor; presenting a pre-selected series of questions to the patient, and capturing the patient's answers; and transmitting the data and patient answers to a remote monitoring system and/or monitoring staff, as described in greater detail below. Preferably, the processor is also capable of comparing the data captured from the sensor with a preset target value, e.g. comparing the captured data with preset minimum and maximum values; receiving instructional data from the remote monitoring system and effecting changes in the stored target value, minimum and maximum values, and question series presented to the patient in accordance therewith. Optionally, the processing means is further capable of presenting the captured data and any variation from the target value to the patient; detecting and verifying proper operation of the system (self diagnostics); and accepting and verifying a patient's id code or passcode, and employing the questions, target value, and minimum and maximum values appropriate to the identified patient. Preferably, the processing means includes no component which would allow a patient to self-analyze the collected data.

The next element of the subject interface system is the communication means, which serves to transmit data to, and receive data from, a remote monitoring system. As such, the communication means comprises both an output means for transferring the collected and processed data to a remote monitoring system and an input means for receiving instructional data from a remote monitoring system. The output and input means of the communication system may be combined as a single component or present as two separate components. The communication means will be any device or system capable of transmitting the data (measured parameters and patient answers) to the remote monitoring system, physician or staff, and receiving data (new target values, questions) from the remote monitoring system, e.g. for storage. Suitable communication means include modems, cable modems, LAN or WAN connections, radio/microwave and other wireless transmitter systems, and the like.

The input means will generally comprise a serial or parallel port to the processor means, but may alternatively or additionally comprise a keyboard or numeric pad, disc drive, and the like. In general, the input means is used by the physician or staff member to effect changes in the system's programming, for example altering the target value, changing the question series, or selecting an alternate question series or language. Alternatively, the input means may be identical with the interrogation means, e.g., the monitoring staff may use the patient's keyboard or keypad to enter changes, or may use the patient's microphone to enter voice commands or a verbal question series. In such cases, the system may be provided with a password, key, or voice recognition system to restrict access to the physician's programming mode" to the monitoring system and/or authorized staff. More preferably, however, the input means provides for remote entry of commands and data by the monitoring staff, and may be identical with the communication means, employing codes or passwords to distinguish authorized access from unauthorized access.

In using the subject interface system, the patient may activate the system by standing on the scale, by physically turning on the system, or by entering a passcode on the patient data input means, e.g. the input panel. If the patient's environment is relatively free of interference (for example, the patient does not live with small children or pets that are likely to activate the system by accident), it is preferred for the system to activate automatically once the patient stands on the scale. If more than one patient is to use the same system, it is preferred for each patient to have a separate ID code or passcode, used to activate the system. If desired, the code may be embedded in a magnetic card, so that the patient need only swipe the card through a reader, or press the card against a designated location on the system. Otherwise, the system may be provided with a simple "on/off" switch, preferably one which may shut off spontaneously after a predetermined period of inactivity.

The series of questions asked of the patient is preferably modified based on the patient's answers. For example, the patient may be asked if he or she ate a meal prior to being weighed. If the patient answers affirmatively, the patient may then be questioned about the size of the meal. If the patient answers negatively, he or she may be questioned about the length of time elapsed since the last meal (or the approximate time of the last meal). The patient may be asked if the correct medication was taken in a timely manner: if so, the processor proceeds on to the next topic; if not, the processor may begin a series of questions to determine why the medication was skipped (e.g., unpleasant side effects, advised by monitoring staff or staff member to discontinue, "just forgot," etc.).

The period of time which elapses between transmission of patient data from the subject interface system to the remote monitoring system will be one that is acceptable in view of the condition being monitored. For example, with cardiac associated diseases, an acceptable period of time may range from about 5 minutes to 1 week. The subject invention will now be further described in terms of the figures. In one embodiment of the invention, as shown in FIG. 1, scale (10) provides a digital output to processor (20), which calculates the difference between the patient's weight and the preset target weight, and outputs the difference on display (40). The scale element (10) is suited for placement on the floor, while the remaining components are best placed on a desk or table. If the processor detects that the weight indicated by the scale is below a preset minimum weight (or above a preset maximum weight), the processor does not initiate the question sequence, and optionally displays a warning (e.g., "Unauthorized Use") on display (40). The processor then presents a series of predetermined questions to the patient through display (40) and/or speaker (80). The patient then responds by keying in answers on keyboard (30), while processor (20) records the answers. The keyboard has three buttons: Y=yes; N=no; and M=maybe (the buttons good represent different conditional gradations, such as "good," "better" and "worse," etc.). At the completion of the question series, processor (20) transmits the recorded answers through communications link (60) to the monitoring staff (70). The monitoring staff, upon examining the answers and data, may then alter the question series and/or download new questions, target values, and minimum and maximum values, consistent with his or her evaluation of the patient's health.

In operation, the patient steps onto scale portion, which automatically activates the processor. The processor compares the weight measured by scale portion with the minimum and maximum weights stored in memory. The minimum and maximum weights are set so that a person or animal much lighter or heavier than the patient will not activate the system inadvertently by stepping onto the scale. If the measured weight falls within the range defined by the minimum and maximum weights, the processor compares the measured weight with the patient's target weight, as established by the patient's physician. The measured weight and deviation (if any) from the target weight is displayed on visual display, and is stored for later transmission to the monitoring staff. The system may also display a greeting, such as by visually displaying "Good morning <patient's name>". Preferably, the system also issues a "spoken" greeting through a speaker, e.g., "Good morning, <patient's name>, are you ready to begin?"The system then presents the predetermined questions selected by the patient's physician, designed to elicit the state of the patient's condition. The patient responds by pressing the button that corresponds to the desired answer, or, optionally, the patient simply speaks his or her responses into microphone. The processor records the answers, whether from button or microphone. Once the series of questions and answers is completed, the processor optionally informs the patient that the questions are completed (visually and/or aurally), and transmits the measured data and patient's answers to the monitoring staff via modem (contained within a base). While connected to the monitoring staffs computer, the answers and data are examined by the monitoring staff (or compared immediately by the monitoring staffs computer), and new questions, target value, and minimum/maximum values are downloaded to the processor. For example, if the patient's responses indicate developing intolerance to the medication prescribed, the new set of questions may include questions designed to identify the symptoms and severity of the intolerance, so that the physician can tell if the patient adjusts to the medication, or if a different medication will need to be substituted.

As discussed above, the subject interface system is useful in the remote monitoring of a diverse number of different patient conditions. For example, the subject interface system finds use in the monitoring of drug titration where a physiological parameter can be measured and related to the effect of a drug that is being self-administered, e.g. insulin, anticoagulants, ACE inhibitors, P-blockers, and the like. Of particular interest is the use of the subject invention in the remote monitoring of cardiac associated diseases, such as HF, where of particular interest is the embodiment of the subject invention comprising a means for measuring edema of a patient extremity as the sensor. Various means for measuring edema are described in detail below.

Also provided is a complete remote monitoring system which includes both the subject patient interface system in operational combination with a remote monitoring means or device. A number of different remote monitoring devices are known in the art and may be operationally linked with the subject patient interface system, as described in U.S. Pat. Nos.: 5,601,435; 4,418,700; 4,566,461; and the like, the disclosures of which are herein incorporated by reference.

EDEMA SENSING MEANS AND METHODS

The present invention provides a patient interface system, as described above, wherein said system comprises a means for measuring edema in the patient. Any known means for detecting and measuring edema (i.e., a "edema measuring means") can be used in conjunction with the patient interface system of the present invention, including, but not limited to, volume displacement measurement means; cross-sectional dimension measurement means; pitting measurement means; and circumferential measurement means. The following section provides non-limiting examples of such means.

These means involve a means for measuring a parameter, which is related to edema. Measured parameters include, but are not limited to, displaced media value, cross-sectional dimension value, force profile, and the like. Once a parameter is measured, a subsequent step is to compare the measured parameter to a control value. The control value will be a value which corresponds to the measured parameter in the absence of the edemic state. Where possible to measure the parameter in the absence of edema, such as in the case of pregnancy or surgery when the measurement can be made at an early time in anticipation of later indications of edema, then such non-edemic measurements can be used as a control value. Most often this is not possible as the desirability of edemic measurements is not apparent until the edema is already a problem. In this case, the best indication of the non-edemic control value is simply the lowest value obtained from a series measurements taken over a period of time. If a microprocessor or other computer device is available, then the recording and displaying of the measurements allows an instant graphic display of not only the measured amount of edema but, often more importantly, whether the condition is worsening or improving. The measured displaced media value and the control value will be compared and any difference will be identified.

The presence of a positive difference between the measured value and the control value is then correlated to the presence of swelling in the region of measurement and edema in the patient. Conversely, the absence of a difference or a negative difference may be related to the absence or improvement of the edemic state. Accordingly, the final step of the subject methods is to attribute the presence of a positive difference to the presence of edema in the patient.

The present invention further provides methods for measuring and monitoring a patient for the presence of edema, using the edema measuring means as described herein. The subject methods may be used to make multiple measurements over a given period of time so that the progression of the edemic state may be monitored. Where multiple measurements are made, the measurements will typically be made according to a schedule, where the measurements may be made hourly, daily, weekly, monthly and the like. In some embodiments, the invention provides methods for remotely monitoring a patient(s), comprising measuring edema in the patient(s), thereby obtaining data relating to the presence of and/or degree of edema, processing the data to determine the degree of edema, and communicating the processed data to a remote monitoring location.

Volume Displacement Means and Methods

The first step in an exemplary volume displacement method is to introduce at least one lower extremity into a container having present therein a volume of a displaceable medium. A variety of media may be employed as the displaceable medium. Suitable media include: (a) liquid media, such as aqueous compositions, e.g. water, other physiologically acceptable aqueous fluids, mineral oil, and the like; (b) gaseous media, e.g. air, nitrogen, carbon dioxide, and the like; and (c) particulate or "macro-fluid" compositions, such as compositions of round beads or other particulate like structures, where the particulate like structures will have an average diameter ranging from about 0.02 to 0.50 in (inch), usually 0.05 to 0.50 in and more usually 0.05 to 0.40 in, and will be fabricated from any suitable material, such as plastic beads, ceramic beads, glass spheres, or naturally occurring bead like materials, such as dried beans, e.g. kidney and pinto, and the like, where macrofluids are preferred in many situations for their ease of use and reduced mess.

The nature of the container into which the extremity is introduced will necessarily depend on the particular displaceable medium present therein. Where liquid displaceable mediums are employed, the container may be as simple as a box shaped container having a circular, rectangular, square, irregular or other convenient cross-sectional configuration and open at the top so as to be capable of receiving the extremity into the interior thereof. Conveniently, such a container may have a scale present on one or more sides thereof to facilitate the rapid determination of the displaced fluid volume, as described in greater detail below. Alternatively, a more complicated configuration may be employed where a gaseous medium is employed as the displaceable medium. In such instances, the container will generally be a sealable container so that upon introduction of the extremity into the container, an increase in pressure of the gaseous medium results. Exemplary containers are further described in terms of the figures below.

Introduction of the extremity of the host into the container results in displacement of a portion of the displaceable medium. The next step in this method is therefore to measure or quantitate the amount of the medium which is displaced and to assign a value to this amount based on the measurement. Any convenient means of measuring the amount of displaced medium may be employed, where the specific methodology employed will necessarily depend on the specific nature of the medium. Thus, where the displaceable medium is a liquid, the amount of displaced medium can readily be measured by using a container having a graduated scale, where the original volume value of the medium prior to introduction of the extremity is subtracted from the new value as measured with the extremity submerged in the liquid. In such embodiments, it is useful to have the graduated scale located on the container in a region of reduced cross-sectional area as compared to the region of the container housing the extremity, since the change in volume will be magnified in such a region and therefore easier to assess.

Where a "macro-fluid" or particulate composition is used as the medium, one can use a similar method where one has a container with a graduated scale. Thus, by using a container of constant volume and a constant amount or number of beads, one first obtains an initial value of the beads in the container without the extremity. Next, the beads are removed and the extremity is introduced into the container. The beads are then reintroduced and the original volume value is subtracted from the new volume value. The resultant difference is the amount of medium displaced is then related to the volume of the extremity. Alternatively, one has the opportunity to use a "counting" method in which the number of beads needed to fill the container is first determined, followed by removal of the beads and introduction of the extremity, followed by reintroduction of a sufficient number of beads to again fill the container. The difference in the number of beads needed to fill the container with and without the extremity present therein is then determined, where means of determining the difference include weighing the beads or counting the beads, e.g. with a bead flow sensor, and the difference is related to the amount of the medium displaced. Prior to each measurement, the macro-fluid may be agitated to ensure adequate packing of the material in the container.

Where a gaseous medium is employed, the gaseous medium will generally be present in a sealable container. The sealable container is one that is capable of receiving the extremity and forming a seal around the extremity to thereby trap the gaseous medium in the container around the extremity. A variety of container configurations may be employed, where suitable configurations will be those in which the extremity is inserted into an opening which then seals around the extremity. Representative structures are further discussed in terms of the figures below. A variety of gaseous media may be employed, as described above, where air is a preferred medium.

The amount of gaseous medium displaced upon introduction of the extremity into the sealable container may be measured a number of different ways and related to the volume of the foot. Typically, the amount of displaced medium will be measured indirectly by looking at changes in parameters related to the volume of the gaseous medium that is displaced, e.g. changes in volume of the container and changes in pressure in the container. Two convenient ways of measuring the amount of displaced gas are the variable pressure mode and the variable volume mode. In the variable pressure mode, the extremity, e.g. the foot, is sealed in the container and the internal pressure of the container is raised to a preselected value that is greater than atmospheric pressure. The volume of the container is then decreased by a preselected amount with a volume modulation means, e.g. a piston. The resultant increase in pressure is then recorded, and the recorded value is used to ultimately derive the volume of the extremity in the container. In the variable volume mode, the extremity is again sealed in the container and internal pressure of the container is raised to a preselected pressure that is greater than atmospheric pressure. A volume modulation means, e.g. a piston, is then used to decrease the volume of the container. When the pressure in the container exceeds the initial pressure by a preselected amount, the volume change is recorded and used to ultimately derive the volume of the extremity in the container.

Figure 2:
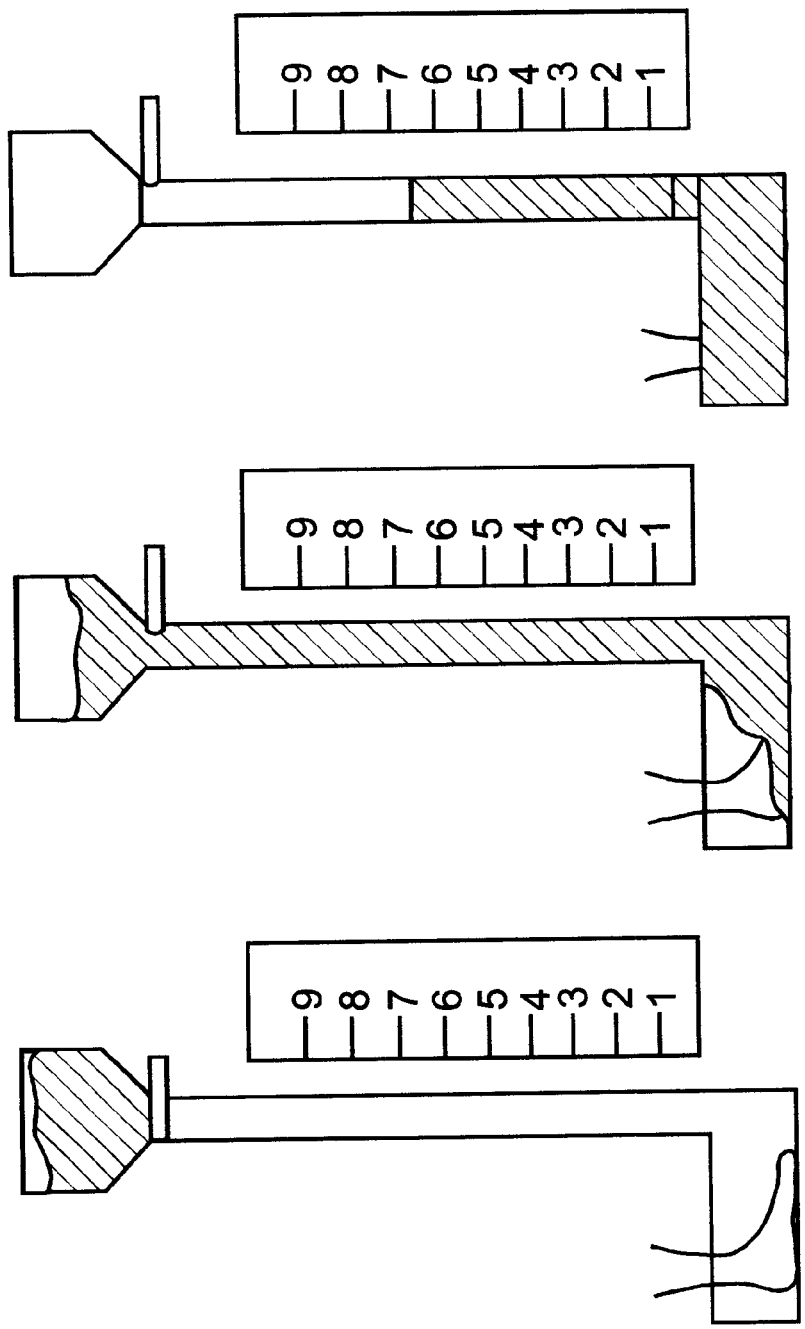
FIGS. 2A to 2C provide a depiction of a method of detecting edema in which the displaceable medium is a particulate composition or "macro-fluid."

Turning now to the figures, FIGS. 2A to 2C depict a representative use of a macro fluid medium, e.g. beads, to determine the presence of edema. A volume of beads is first introduced into an empty container and the level to which the beads reach in the column is recorded. The beads are then removed and a foot is introduced into the container, as shown in FIG. 2A. The beads are then reintroduced into the container as shown in FIG. 2B. The level to which the beads reach when the foot is present in the container, as shown in FIG. 2C, is then recorded. The difference in level values in the presence and absence of the foot in the container is then related to the volume of the foot. The scale is located in a region of reduced cross-section area in order to provide for easier reading of the amount of change, since the change is amplified in this region.

In FIG. 4 is depicted an embodiment in which air is employed as the displaceable medium. In FIG. 4 the container comprises a bladder of air as the floor. When the foot is placed in the opening and onto the bladder, the bladder compresses resulting in inflation of a torrus shaped bladder around the ankle. The torroidal shaped bladder conforms to the ankle and seals a fixed mass of air around the foot inside the box. In some embodiments, the torroidal bladder will take all of the air from the lower chamber and expand from condition A to condition B. In other embodiments, the torroidal bladder may leak into the chamber and form a seal but not distend to the full volume of the lower chamber. The torroidal bladder may be fitted with apertures to permit gas to move into the chamber surround the foot so as to maintain sufficient pressure around the ankle to minimize leaking. The box can then be pressurized and depressurized as required, either through an additional aperture or through the torroidal bladder. Optionally, the torroidal bladder can be inflated with a mechanical pump.

Figure 4A:
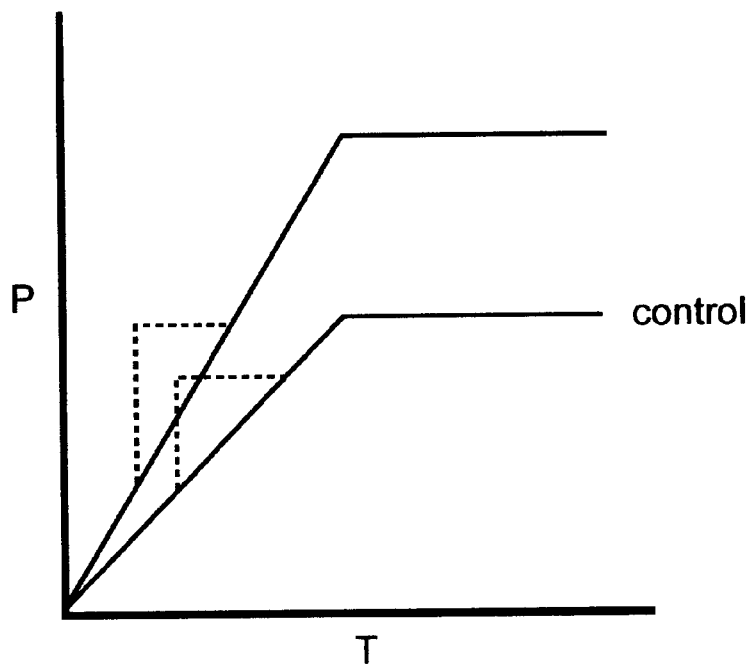
FIGS. 4A & 4B are graphs of the pressure vs. time derived from data obtained from a device as shown in FIG. 3.
Figure 4B:
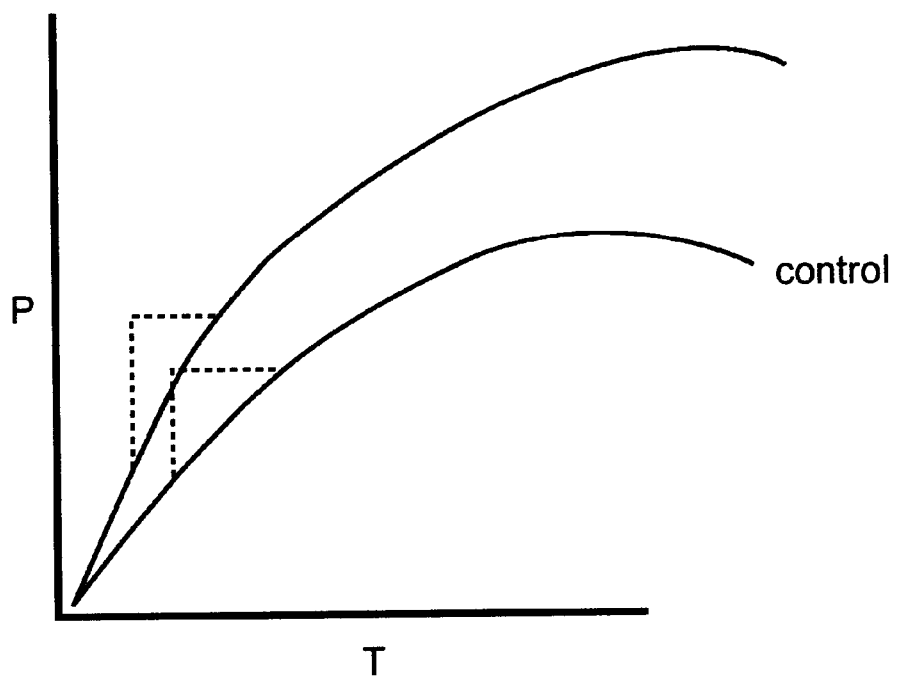

With this embodiment, air from the bladder can be used for both inflation of the cuff and pressurization of the container housing the extremity. The measurement of pressure can be made by either measuring the final pressure or measuring the pressure differential of the box over a given period of time, i.e. looking at the change in pressure over a given period of time. These methods can be used in situations where the cuff either makes a perfect seal or imperfectly seals the container such that there is a leakage of gaseous medium from the container. If a perfect seal is achieved, one can measure the pressure over a period of time and plot the results in a graph as shown in FIG. 4A. If an imperfect seal is achieved, the pressure over time can still be plotted to obtain a graph as shown in FIG. 4B. In either method, one can then derive slope values for a selected region of the line and compare these values to obtain measurements from which the edemic state of the extremity can be derived.

Alternatively, the foot could be placed into a container having a thin, airtight sock. An iris analogous to the aperture of a camera would then close around the top of the sock and the foot. Upon pressurization, the sock is forced tightly around the foot. The iris prevents parts of the sock from being pushed out the top of the box by the increased pressure.

Cross-Sectional Dimension Measurement Means and Methods The first step of a cross-sectional method is to measure a cross-sectional dimension of a limbic extremity of the mammalian host, e.g. human patient. Generally the limb that is measured is a lower extremity or region, portion or location thereof, where usually the cross-sectional dimension of at least one of the ankle and foot are measured. In this exemplary method, the cross-sectional dimension of only a single region, portion or location of the limb may be measured, or the cross-sectional dimension of a plurality of locations may be measured, where when a plurality of locations are measured, usually the number of different locations that are measured will not exceed three, and more usually will not exceed two.

The cross-sectional dimension that is measured may be the diameter, radius or cross-sectional area of the extremity at a selected location, where preferred cross-sectional dimensions are the diameter and the cross-sectional area.

Figure 7A:
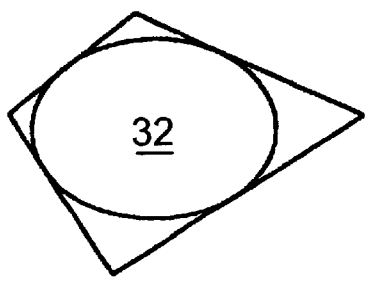
FIGS. 7A and 7B shows how four lines can enclose a non-circular limb and the four circles that can be derived therefrom.
Figure 7B:
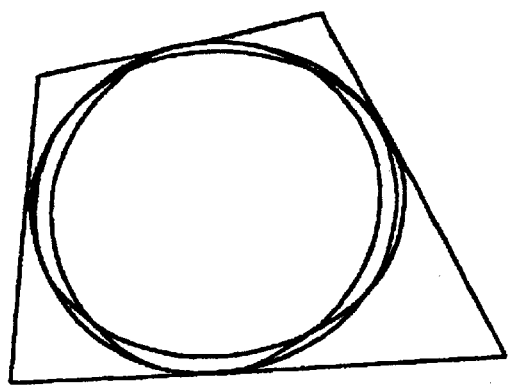
Figure 8A:
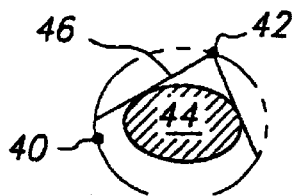
FIGS. 8A to 8F depict a device for measuring a cross-sectional area.
Figure 8B:
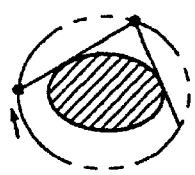
Figure 8C:
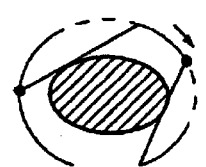
Figure 8D:
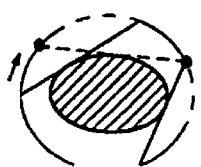
Figure 8E:
Figure 8F:
Figure 10A:
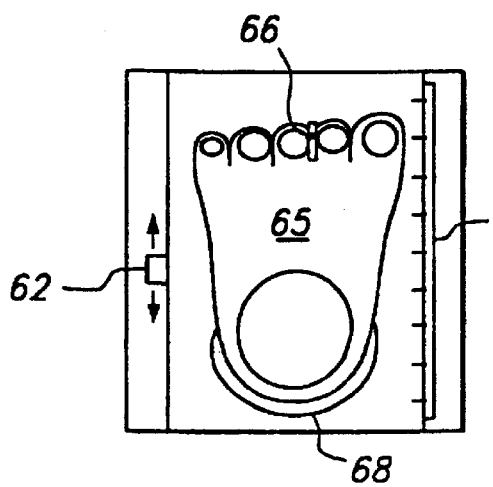
FIGS. 10A & 10B depict a device for measuring a cross-sectional dimension.
Figure 10B:
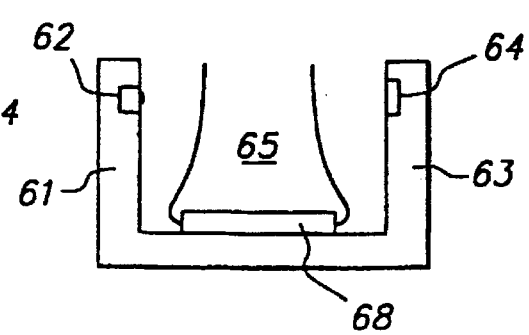

For measuring the cross-sectional dimension, a measuring device that is capable of providing at least an approximation or measurement of the limb cross-sectional dimension is employed. Preferably the device is simple, inexpensive, and able to provide data that can readily be input into a microprocessor. The nature of the device used to measure the cross-sectional dimension will necessarily depend on the particular cross-sectional dimension to be measured.

Where the cross-sectional dimension to be measured is the diameter of the extremity at a particular location, one may use a device comprising a light detector and light source as depicted in FIG. 10A and 10B. As shown in FIG. 7A and 7B, the device consists of two towers, 61 and 61, one of which has a movable photodetector 62 and the other of which has a light source 64 running the length of the device. The light and detector will be configured such that the detector detects only light that is perpendicular to it. As such, a light columnator will be employed, where the columnating means may be part of the detector and or the source. For example, the columnator could be an extended thin tube attached to the source or the detector. Alternatively, the light source could be a point source that moves with the detector such that when the limb is between the source and detector, the detector detects no light from the source. In using the device to determine the diameter of an extremity, the extremity (e.g. a foot, as shown in the FIGS. 10A & 10B) is placed between the light detector and the light source. The moving detector is then moved back and forth along the length of the extremity at the location of interest for which a diameter measurement is desired and points of transition between light and dark are recorded. From the recorded data, the diameter of the extremity is determined. To ensure that an accurate measurement is obtained each time, the device may further comprise a reference means for ensuring that the extremity is placed between the light source and the detector at the same location each time a measurement is taken. For example, where the extremity is a foot 65, the device may further comprise a heel counter 68 and a toe alignment means 66, as shown in FIG. 10A & 10B.

Where the cross-sectional dimension is the area of the extremity, a variety of different methods of determining the cross-sectional area of the extremity may be employed. One method of determining the cross-sectional area of the limb is to impose at least three distinct, non-parallel tangent lines on the periphery of the limb. In this method, at least three tangent lines will be imposed, where the number of tangent lines may be much higher, as discussed below. From the tangent lines, a series of circles is derived (the number of circles that can be derived equals $n!/(3!*(n-3)!)$ or $_nC_3$ where n is the number of lines or points, e.g. for 1 line, 0 circles; for 2 lines, 0 circles; for 3 lines, 1 circle; for 4 lines, 4 circles; for 5 lines, 10 circles . . . ). The areas of these circles is then compared, e.g. averaged or otherwise compared, to arrive at value that approximates the cross-sectional area of the extremity.

A device for measuring the circumference of an extremity through the production of at least three tangent lines, as described above, is depicted in FIGS. 8A to 8F. The device has a light 40 and a detector 42, both of which are capable of independently moving around the periphery of the extremity 44 at roughly the same vertical height. In using this device to produce at least the three requisite tangent lines, the extremity will first be introduced and the light and detector positioned relative to one another such that the detector is in the shadow of the extremity. The detector is then moved around the circumference of the extremity, while maintaining the light source in a constant position, until the detector emerges from the shadow of the extremity and registers light from the light source. The absolute position of both the detector and the light source are then recorded. The light source is then moved along the circumference, while maintaining the position of the detector, until the detector is again in the shadow of the extremity. The detector is then moved while maintaining the position of the light source until the detector again registers light from the light source. The absolute positions of the light source and detector are again recorded. In this manner, a series of at least three tangent lines is produced at different positions of the periphery of the extremity. The produced tangent lines are then use to determine the periphery of the extremity.

Figure 9:
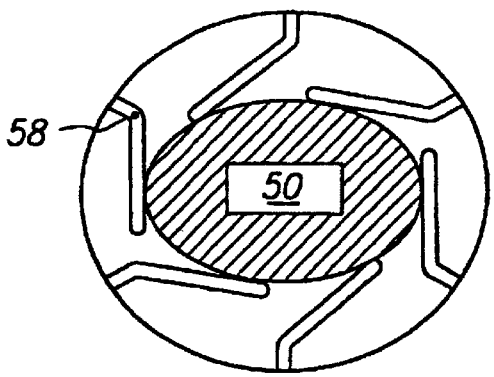
FIG. 9 depicts a device for measuring a cross-sectional area.

Alternatively, the device depicted in FIG. 9 can be used to impose the series of tangent lines from which the cross-sectional area is derived, as described above. In FIG. 9, the surface of the extremity 50 is contacted at a plurality of distinct locations on the periphery with a plurality of positional sensors 58. By plurality of positional sensors is meant at least 3, usually at least 4 and more usually at least 5, where the number of different positional sensors may be as high as 8 or more, but will usually not exceed 7 and more usually will not exceed 6. The sensors are used to determine the angle at which the member contacts the limb and thus the equation of the line represented by the member. The sensors may be any convenient sensors capable of providing positional information or data to a processing means which in turn is capable of deriving the circumference of the extremity from the positional information or data. Representative sensing means include: piezo-films, strain-gages, angular potentiometers, encoders, and the like. The sensors may be positioned on an extender means, as shown in FIG. 9, where the extender means may be fabricated from compliant material such that the extremity can easily be positioned, or be fabricated from a more rigid material, in which case the device will provide for the extenders to be retracted from the extremity surface upon introduction and removal of the extremity.

If a large number of distinct tangential lines are imposed on the periphery of the limb, where by large number is meant greater than about 30, a polygon can be derived therefrom. The cross-sectional area of the circle can then be derived from the polygon.

Figure 5A:
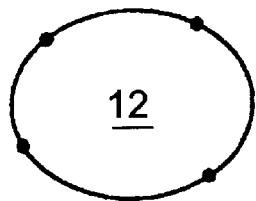
FIGS. 5A & 5B depict four points of a non-circular limb and the four circles that can be derived therefrom.
Figure 5B:
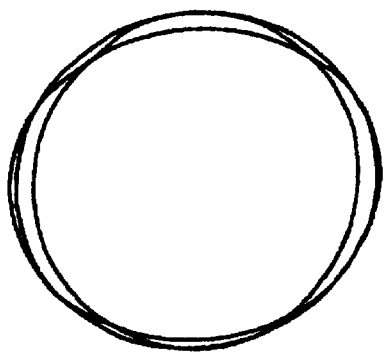

Instead of using a series of tangent lines to obtain the cross-sectional area of the limb, a series of at least three distinct points falling on the periphery of the extremity can be employed. FIG. 5A shows a limb having four points selected on the periphery thereof. From the four points, a series of four circles can be derived. FIG. 5B. The areas are then averaged to obtain the cross-sectional area of the limb.

Figure 6:
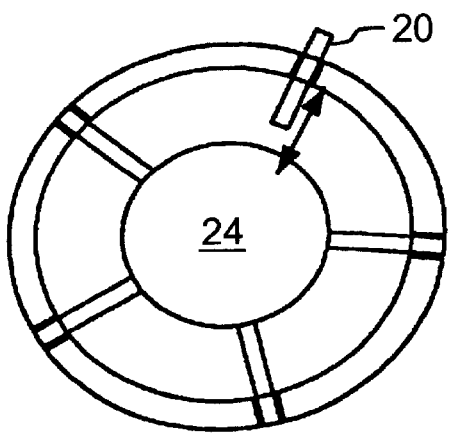
FIG. 6 shows a device that can be used to measure the cross-sectional area of a limb.

A device for determining the cross-sectional are using at least three distinct points is depicted in FIG. 6. In the device of FIG. 6, a plurality of linear actuators 20 are positioned around the periphery of the limb 24 and are capable of radially inward or outward from the limb. Positioned at the end of each actuator is a micro switch or contact sensor. The position of the actuator end is determined by the position of the actuator bushing and the distance the actuator is protruding. Encoders, linear potentiometers or other methods can determine this distance.

In other embodiments, other higher order analytical shapes, e.g. ellipses or other conical shapes, are derived from the points or tangent lines and used to derive the cross-sectional area of the limb.

Pitting Measurement Means and Methods

Methods for sensing edema can be carried out using the following exemplary device. Such a device may comprise a planar surface having a force probe extendable therefrom. The planar surface will generally be a plate or other similar structure, where the plate like structure may be configured in a variety of different shapes, such as a square, rectangle, circle, oval or other suitable shape. Plate like structures are suitable for use in situations where one desires to contact only a partial region of the extremity. Alternatively, the planar surface may be the inner surface of a cuff or other similar structure which surrounds the extremity in the region of interest. The planar surface may be the surface of a number of distinct materials, including metals, such as aluminum, stainless steel and the like, or more pliant materials, such as polymeric materials, e.g. synthetic foam materials, Delrin, polyethylene, teflon, naturally occurring materials, e.g. rubber, wood, and the like.

In addition to the planar surface, a suitable device comprise a probe extendable from the planar surface of the device. Conveniently, the planar surface will comprise an orifice or opening, usually in a central region of the planar surface, from which the probe is extendable. The probe comprises a force sensor, where any convenient force sensor capable of collecting force data and relating it to a processing means (in those embodiments comprising a processing means) may be employed. Suitable types of force sensors which the probe may comprise include: loadcells (as described in U.S. Pat. No. 5,370,535, the disclosure of which is herein incorporated by reference), spring activated adjustable force sensors with microswitches, and the like.

Figures 12A, 12B:
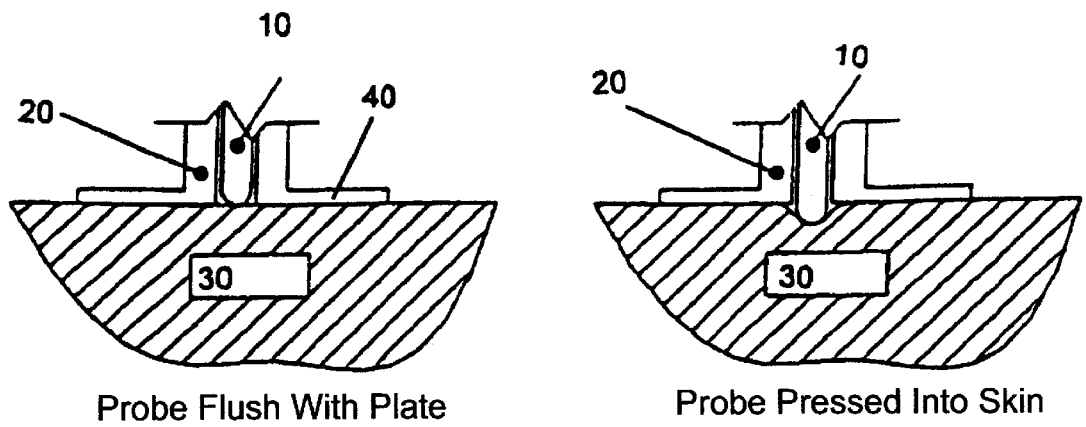
FIGS. 12A and 12B show a force sensor means and its use.

A representative device suitable for use in detecting edema is shown in FIGS. 12A and 12B. The device comprises a planar surface 40 of a plate component 20 and a probe 10 which extends from the planar surface towards the skin 30 during use, as explained in greater detail below.

In addition to the above components, the device may further comprise a number of additional components which assist in the measurement and/or generation of the force profile, as described below. One such element is a second plate or similar structure which is opposite the planar surface that serves a reference for the probe, e.g. in a C-clamp fashion. The device may also comprise a processing means for generating a force profile from the gathered measurements. Other elements that may be included in the device are: motors, such as a stepper motor, etc.

In using the above-described device, the first step of the subject methods is to contact a region of the extremity with the planar surface. The amount of pressure applied upon contact should be sufficient to keep the planar surface in a constant location in relation to the limb, yet not so great as to depress the planar surface below the surface of the extremity. Suitable contact can be achieved a number of different ways, depending on the particular device configuration being employed. For example, the host may simply press the extremity lightly against the planar surface. Alternatively, the device comprising the planar surface may have a second plate positioned opposite the planar surface, between which the extremity is placed and which may be tightened in a C-clamp fashion to provide for the requisite contact. In yet another embodiment where the device is in the form of a cuff that surrounds or encircles the extremity at the region of interest, the cuff may be tightened a sufficient amount to provide for a tight fit and the requisite contact.

After sufficient contact between the planar surface and the extremity is achieved, the probe comprising the force sensor is then extended from the planar surface against the extremity surface resulting in the production of a "pit" in the surface of the extremity. The force employed to extend the probe will be sufficient to generate the depression or pit and will generally range from about 0.1 to 4.0 cm, usually from about 0.3 to 3.0 cm and more usually from about 0.2 to 2.0 cm. The rate at which the probe is extended will vary between about 0.25 and 4.0 cm/sec, usually from about 0.5 to 2 cm/sec . The probe will continue to be pressed against the surface of the skin of the extremity until a predetermined force is reached, where that force will generally range from about 0.1 to 5.0 kg, usually from about 0.2 to 3.0 kg and more usually from about 0.5 to 2.0 kg. Once the predetermined and specified force is reached, the probe is maintained for a period of time at a constant position relative to the extremity and the planar surface of the device, during which time a plurality of force measurements are recorded. The period of time contact is maintained will be sufficient to perform the desired number of force measurements, where generally the period of time will range from about 1 to 20 seconds, usually from about 2 to 10 seconds and more usually from about 3 to 5 seconds. The number of force measurements taken during the period of time will be sufficient to obtain suitable number of data points to generate a sufficiently detailed force profile, as described in greater detail below, and will be at least 1, usually at least 2 and more usually at least 5 and may be great as 20 or greater, but will usually not exceed 10 in number.

The above steps result in the generation of a series of force measurements over time. This force measurement data is then forwarded (e.g. transferred, transmitted, etc.) to a processing means to which the data is forwarded from the sensor and which derives the force profile from the data. The processing means may be part of the device or part of a monitoring system that is operationally linked to the device, e.g., a monitoring system as described herein.

Circumferential Measurement Means and Methods

In these methods, the first step is to measure the perimeter of a limbic extremity of the mammalian host, e.g. human patient. In measuring the perimeter, the distance around a region of the limb, i.e. the circumference, is determined. Generally the limb that is measured is a lower extremity or region, portion or location thereof, where usually the perimeter of at least one of the ankle and foot are measured. In these methods, the perimeter of only a single region, portion or location of the limb may be measured, or the perimeter at a plurality of locations may be measured, where when a plurality of locations are measured, usually the number of different locations that are measured will not exceed three, and usually will not exceed two.

For measuring the perimeter, a measuring device that is capable of providing an accurate measurement of the limb perimeter is employed. Preferably the device is simple, inexpensive, and able to provide data that can readily be input into a microprocessor. Of particular interest in the subject invention is the use of cable extension transducer devices for perimeter measurement. Ideally, the transducer devices are easily handled, typically having a length ranging from 2.5 to 3.5 in, a height ranging from 1.5 to 2.0 in and a width ranging from 1.75 to 2.75 in. Preferably, the devices are also lightweight, having an weight that does not exceed 100 g and usually does not exceed 80 g.

A variety of cable extension transducer devices are known and suitable for use in the subject methods. Cable extension transducer devices are described in U.S. Pat. Nos. 5,236,144 and 5,560,118, the disclosures of which are herein incorporated by reference. Cable extension transducer devices are available from a number of different commercial sources, including: Unimeasure (Corvalis, Oreg.); SpaceAge Control, Inc. (Palmdale, Calif.); Celesco Transducer Products, Inc. (Canoga Park, Calif.); Patriot Sensors & Controls Corporation (Simi Valley, Calif.); and the like.

Figure 13:
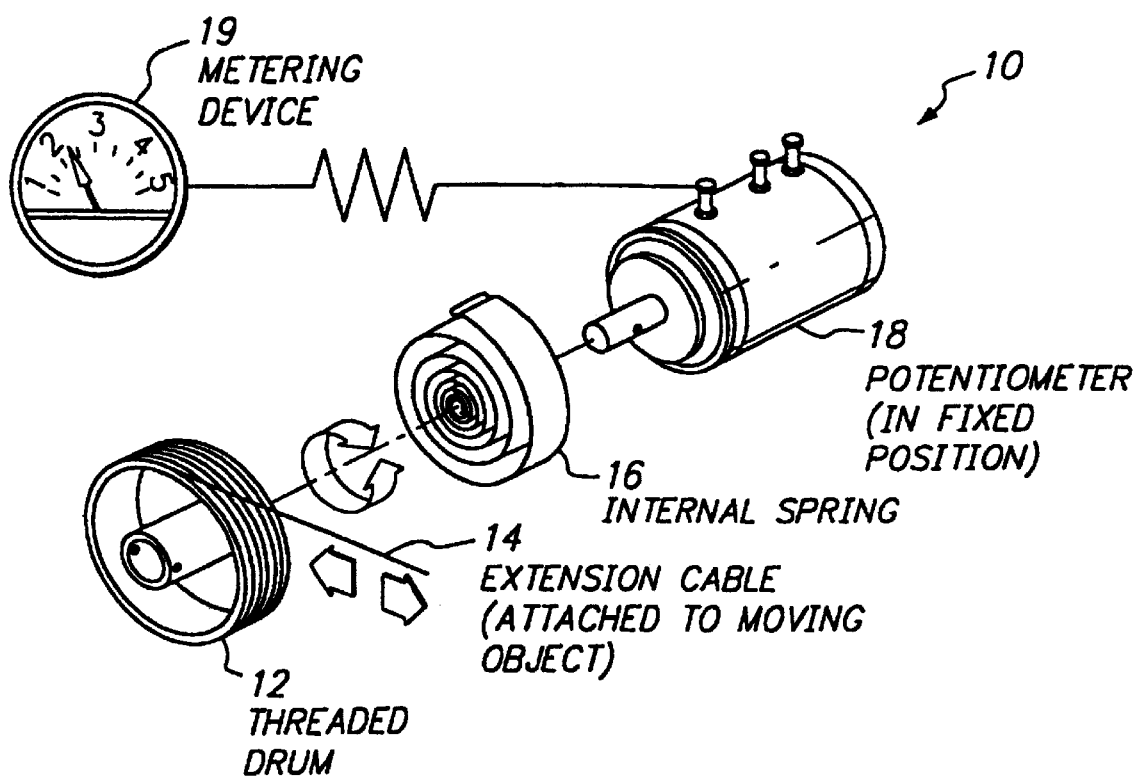
FIG. 13 provides an exploded view of a cable extension transducer suitable for use in the subject invention.

Cable extension transducer devices suitable for use in the subject invention can be configured in a variety of different ways. In one suitable embodiment, the transducer comprises a cable extension attached to a rotary shaft that is, in turn, attached to a precision potentiometer. This embodiment is shown greater detail in FIG. 13, which provides an exploded view of such a device. In the device shown in FIG. 13, device 10 comprises a threaded drum 12 around which is wound an extension cable 14. The device further comprises an internal spring 16 and a potentiometer 18 and is connected to metering device 19. In this embodiment, the extent to which the cable is extended is transduced to a resistance value, which value can then be correlated back to a length value. In an alternative embodiment, the cable extension is attached to a rotary shaft encoder and the device further comprises a digital counter that is capable of counting the pulses provided by the encoder. The extent to which the cable is extended during measurement is then transduced into a digital readout.

Cable extension transducer devices suitable for use should have cables fabricated from suitable flexible materials so that the cable can be snugly wrapped around the portion of the limb being measured in a manner where excessive compression of the flesh is avoid.

In using cable extension transducer devices to measure the perimeter of the limb, first a location of the lower extremity will be selected, e.g. the ankle, the foot and the like. The cable is then wrapped around the circumference of the limb at the location of measurement, with care taken to ensure the cable is sufficiently taut to eliminate any air spaces between the limb tissue and the cable, but not so excessively taut such that the cable compresses into, and depresses below, the surface of the flesh.

In using cable transducer devices for measuring the perimeter, it is preferable to base the perimeter value on the length of cable directly in contact with the tissue, i.e. to only use the cable distance beginning from the actual point of contact with the skin to the end of the cable and exclude that portion of the cable distance extending from the device to the skin. Put another way, the end of the cable that is wrapped around the limb should attach directly to the cable at the point where the cable initially contacts the skin from the device, and not at a region of the cable closer to the cable outlet of the device, since contacting at the latter region would result in the presence of an "air-gap" which would provide a potential source of error in measurement.

One way to ensure that the measured distance is derived directly from cable actually contacting the tissue surface is to use the device in conjunction with a reference rod or other device which allows for a "reverse curve" at the initial point of contact between the cable and the limb, as depicted in FIG. 14. In this embodiment, a reference rod is placed next to the limb tissue at the location where the perimeter is to be measured. Cable exiting the transducer device is first wrapped around the reference rod in a direction counter to the direction it then travels around the limb. By holding the transducer at a constant location relative to the limb, the cable distance between the transducer and the limb is then known and can be treated as a "zero shift" or offset in the measurement determination step.

Instead of using a reference rod, the cable may extend from the transducer device through a tube, as shown in FIG. 15. In this embodiment, the cable extends from the device through a tube and then around the limb, not shown. The end of the cable is then attached to the point of the cable that first emerges from the tube at the point of contact with the skin.

In those embodiments of the invention where multiple measurements are taken of the same region over a period of time, e.g. days, weeks, months or longer, it is critical that the location that is measured be substantially the same for each measurement. One means of ensuring that the substantially the same location is measured each time is to use a transducer device where the location of the transducer is fixed and constant relative to the limb being measured. For example, where the location to be measured is an ankle or foot, a device suitable for use will comprise, in addition to a fixed transducer, a means for ensuring that the foot is always positioned at the same place relative to the fixed transducer. Such means could be as simple as an reference mark, e.g. a foot outline, on a platform that indicates where the foot should be placed. Alternatively, the means could comprise ankle cups, gripping devices and the like, that more stably secure the limb in a fixed position relative to the transducer. Another means of ensuring that the same location is measured is to mark the region to be repeatedly measured with an at least a semi-permanent marking means, such as an indelible ink.

In some embodiments, it may be desirable to make two or more perimeter measurements at different locations. In such embodiments, one may use a portable transducer device which is not fixed at any particular location relative to the limb being measured. Alternatively, one may employ a fixed device comprising two or more transducers positioned at fixed locations relative to different locations of the limb. In yet a further embodiment, one could have a transducer device that comprises two or more cables.

The extent the cable is extended around the limb is then transduced into a perimeter value. The steps taken to transduce the cable extent into a perimeter value will depend on the particular transducer device employed. For example, with the resistance device depict in FIG. 13, the extent to which the cable is extended around the limb is automatically transduced by the device into a certain resistance value. This resistance value can then be used as a perimeter value, or further transduced into actual distance units (or other convenient units) which can then serve as the perimeter value.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celcius, and pressure is at or near atmospheric.

Example 1

Figure 3:
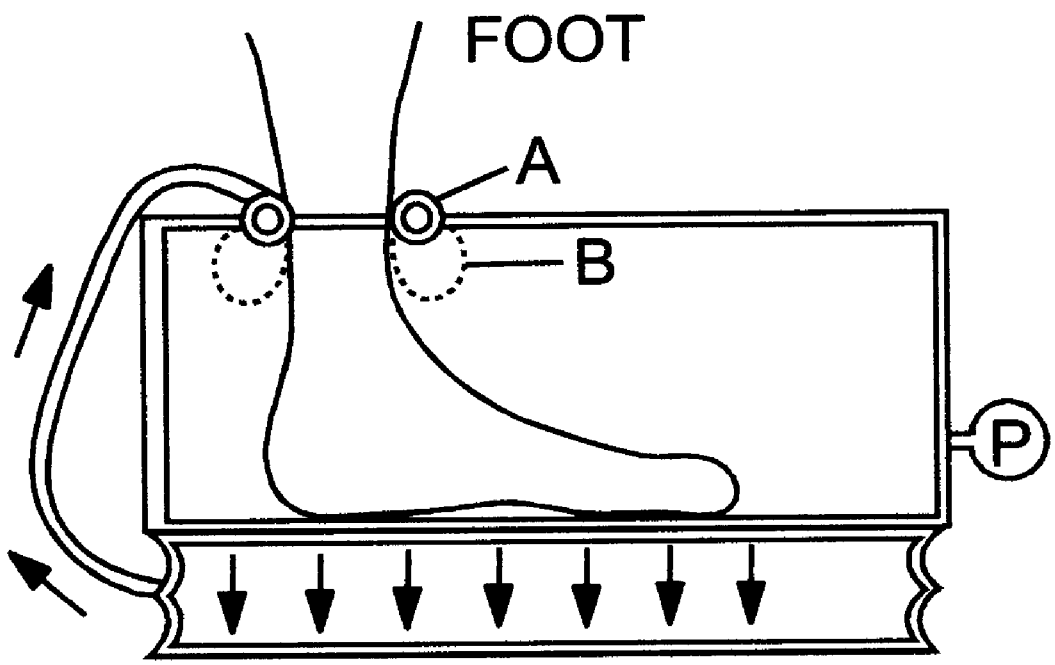
FIG. 3 provides a depiction of a method of detecting edema in which the displaceable medium is a gas.
Figure 11:
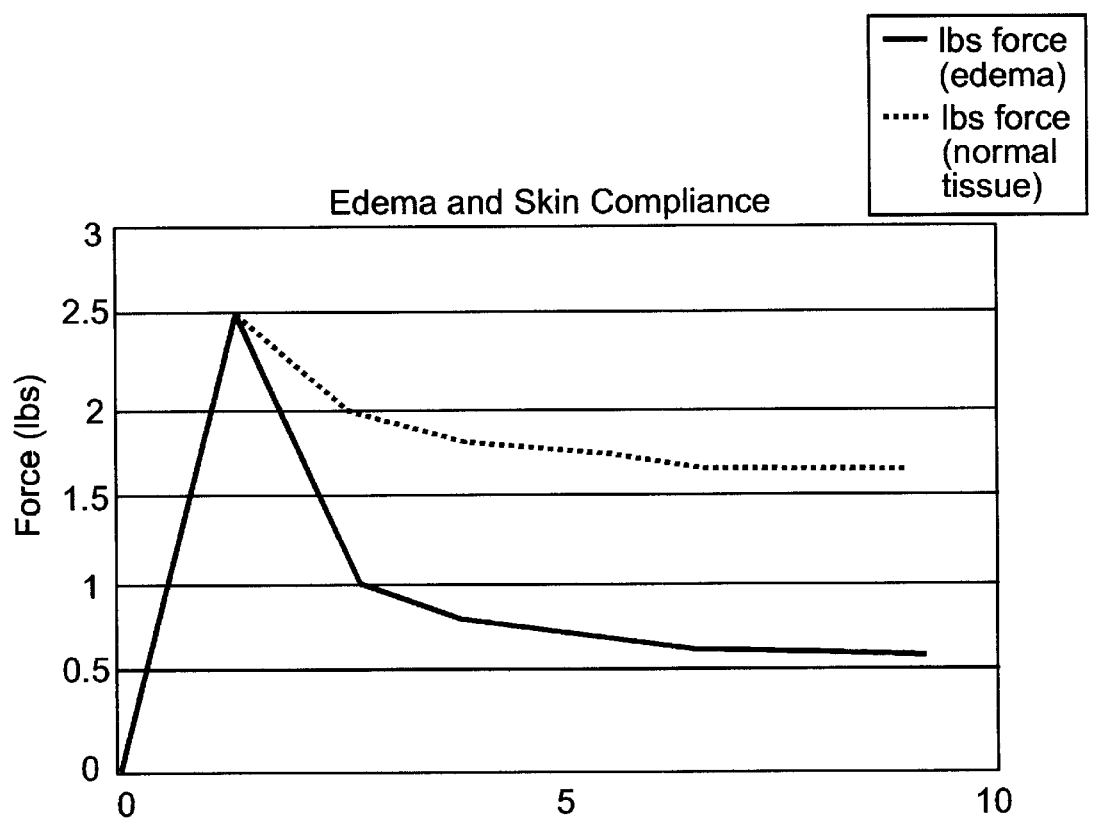
FIG. 11 shows a representative force profile obtained using a pitting measurement device.

A sixty-one year old man with congestive heart failure resides at home with a care giver. A computerized telephonic monitoring system is installed which transmits information to a centralized nursing station. The system requires the patient to complete a daily monitoring cycle which includes answering questions on his general health, sleeping, appetite, and any unusual symptoms.

Where the edema sensing means is a volume displacement measuring means, the patient stands on an electronic scale which records his weight, and while seated on a closed toilet seat or in a low chair places his foot on an indicated location in the device shown in FIG. 3. The patient presses a button to record the measurements and detaches the apparatus. At a later time, the computer system transmits the entire information set collected, including the edema measurements, to the central station.

Where the edema sensing means is a cross-sectional dimension measuring means, the patient stands places his foot on an indicated location on a flat plate attached between a light source and detector, as shown in FIGS. 6A and 6B. The diameter of the foot is determined and, at a later time, the computer system transmits the entire information set collected, including the edema measurements, to the central station.

Where the edema sensing means is a pitting measuring means, the device shown in FIGS. 12A and 12B is employed to generate a force profile as depicted in FIG. 11. The patient presses a button to record the measurements and, following generation of the force profile, removes the apparatus. At a later time, the computer system transmits the entire information set collected, including the edema measurements, to the central station.

Where the edema sensing means is a circumferential measuring means, the patient stands on an electronic scale which records his weight, and while seated on a closed toilet seat or in a low chair places his foot on an indicated location on a flat plate attached to two cable transducers. One cable is secured around his instep, and one cable is secured around his lower leg, as shown in FIG. 14. The patient presses a button to record the measurements and detaches the apparatus.

In a hospital setting, for example when a number of patients are being monitored for edema, a nurse, using a portable cable transducer monitor, visits each patient once a day. After entering each patient's number into the portable monitor, the nurse extends the cable and attaches it around the patient's lower leg at a premarked position, an allows the monitor to record the measurement. Upon the completion of her rounds the monitor is briefly attached to the hospital information system, which updates each patient's file with the measurement. The hospital information system provides the physician with a graphical display of the daily measurement results.

With an analysis of this daily information, a physician has early warning information, and can provide prompt care, avoiding acute episodes.

It is evident from the above discussion that the subject invention makes a significant contribution to the field of chronic condition management. The patient interface system described herein permits the physician to conduct such monitoring economically and rapidly, as it does not require either the physician, nurse or the patient to travel. This interface system both measures physical data and interrogates the patient through a series of simple questions designed to elicit any important changes or factors in the patient's health. Such questions can be used to obtain information that cannot otherwise be practically obtained without very intrusive or expensive monitoring. The subject interface system is also easy to use and should therefore result in better patient compliance and a concomitant increase in the reliability of the data collected and the effectiveness of the treatment regimen provided to the patient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A patient interface system for use in collecting and transferring data from a patient to a remote monitoring system, said system comprising:
   (a) a patient data imput means comprising:
      (i) a means for measuring edema in the patient; and
      (ii) an interrogation means;
   (b) a processing means for receiving and storing data from said patient data input means;
   (c) a communication means for transferring said processed patient data from said processing means to a remote monitoring system and receiving instructional data from said remote monitoring system.

2. The system according to claim 1, wherein the edema measuring means is selected from the group consisting of a volume displacement measurement means, a cross-sectional dimension measurement means, a pitting measurement means, and a circumferential measurement means.

3. The system according to claim 2, wherein said volume displacement measurement means comprises:
   a container comprising a displaceable medium whereby a portion of said displaceable medium is displaced when an extremity of a patient is placed in the medium; and
   a means for measuring said displaced medium and obtaining a measured amount value; and
   a means for relating said measured amount value to the presence or absence of edema in said patient.

4. The system according to claim 3, wherein said displaceable medium is a liquid.

5. The system according to claim 2, wherein said cross-sectional dimension measurement means comprises:
   a means for measuring a cross-sectional dimension of at least one limbic extremity of a patient; and
   a means for relating said value to the presence of edema in the patient.

6. The system according to claim 1, wherein said processing means accepts and stores a new predetermined target value and series of questions from said remote monitoring system.

7. The system according to claim 1, wherein said question and answer means comprises a device selected from the group consisting of a video display and an audio display.

8. The system according to claim 7, wherein said question and answer means further comprises at least one of a keyboard, a plurality of buttons and a microphone.

9. The system according to claim 1, wherein said communication means comprises at least one of a modem, a serial interface, a LAN connection and a wireless transmitter.

10. A patient interface system for use in collecting and transferring data from a patient suffering from a cardiac associated disease to a remote monitoring system, said system comprising:
    (a) a patient data input means comprising:
       (i) a means for measuring edema in an extremity of the patient; and
       (ii) and interrogation means;
    (b) a processing means for:
       (i) receiving and storing data from said patient data input means;
       (ii) storing a predetermined target value and a series of questions;
       (iii) comparing a measured edema value with said predetermined target value to determine a variance; and
       (iv) accepting and storing a new predetermined target value and series of questions from said remote monitoring system; and
    (c) a communication means for transferring said patient data from said processing means to a remote monitoring system and receiving instructional data from said remote monitoring system.

11. The system according to claim 10, wherein said interrogation means comprises a device selected from the group consisting of a video display and an audio display.

12. The system according to claim 11, wherein said interrogation means further comprises at least one of a keyboard, a plurality of buttons and a microphone.

13. The system according to claim 10, wherein said communication means comprises at least one of a modem, a serial interface, a LAN connection and a wireless transmitter.

14. The system according to claim 10, wherein said means for measuring edema is a volume displacement means.

15. The system according to claim 10, wherein said means for measuring edema is a cross-sectional dimension measurement means.

16. The system according to claim 10, wherein said means for measuring edema is a pitting measurement means.

17. The system according to claim 10, wherein said means for measuring edema is a circumferential measurement means.

18. A patient interface system for remote monitoring of a patient, comprising:
    (a) a patient data input means comprising a means for measuring edema in a patient, wherein the edema measuring means is selected from the group consisting of a volume displacement measurement means, a cross-sectional dimension measurement means, a pitting measurement means, and a circumferential measurement means;
    (b) a process means for receiving and storing data from the data input means; and
    (c) a means for communicating data to a remote monitoring system.

19. A method of remotely monitoring a plurality of patients, comprising:
    (a) measuring a first patient at a first location for edema;
    (b) processing data obtained in (a) to determine the degree of edema the patient has;
    (c) communicating the data processed in (b) to a remote monitoring location; and
    (d) repeating (a), (b), and (c) with the first patient and with a plurality of additional patients.

20. The method according to claim 19, wherein said measuring is a pitting measurement method comprising:
    contacting an extremity of the first and additional patients with a device comprising a planar surface and a probe extendable therefrom;
    extending said probe from said planar surface until a specified force is reached, whereby a depression in the skin of said extremity at the site of said extended probe is produced;

maintaining said probe in constant position for a period of time and taking a plurality of force measurements;

generating a force profile from said plurality of force measurements; and relating said force profile to the presence or absence of edema.

21. The method according to claim 19, wherein said measuring is a circumferential measurement method comprising:

measuring the perimeter value of at least one limbic extremity of the patient; and relating the perimeter value to the presence of edema in the patient.

22. The method according to claim 19, further comprising asking the first patient and additional patients a series of questions to obtain data and comparing the data to a predetermined target value.

23. The method according to claim 19, further comprising determining a variance between the data obtained and the predetermined target value.

24. A method for collecting and transferring data from a patient having a condition related to edema to a remote monitoring system, said method comprising:

(a) collecting data associated with said condition by using a means for measuring edema and an interrogation means;

(b) processing said collected data with a processing means; and (c) transferring said processed data with a communication means to a remote monitoring system.

25. The method according to claim 24, wherein said processing comprises comparing said collected data with a predetermined target value to determine a variance, wherein said processing means stores said predetermined target value and a series of questions.

26. The method according to claim 25, wherein said method further comprises changing at least one of said predetermined target value and series of questions in response to said data.

27. The method according to claim 25, wherein said condition is a cardiac associated disease.

28. A method for collecting and transferring data from a patient having a cardiac associated disease to a remote monitoring system, said method comprising:

(a) collecting data associated with said condition by:
  (i) detecting the presence of edema with an edema detection means; and
  (ii) presenting at least one question to said patient and obtaining at least one answer from said patient with an interrogation means;

(b) processing said collected data with a processing means; and (c) transferring said data with a communication means to a remote monitoring system.

* * * * *